United States Patent
Moinet et al.

(10) Patent No.: US 7,034,021 B2
(45) Date of Patent: Apr. 25, 2006

(54) DIHYDRO-1,3,5-TRIAZINE AMINE DERIVATIVES AND THEIR THERAPEUTIC USES

(75) Inventors: Gérard Moinet, Orsay (FR); Daniel Cravo, Sartrouville (FR); Liliane Doare, Viry Chatillon (FR); Micheline Kergoat, Bures-sur-Yvette (FR); Didier Mesangeau, Combs la Ville (FR)

(73) Assignee: LIPHA, Lyons (FR)

( * ) Notice: Subject to any disclaimer, the term of this patent is extended or adjusted under 35 U.S.C. 154(b) by 279 days.

(21) Appl. No.: 10/181,223

(22) PCT Filed: Jan. 25, 2001

(86) PCT No.: PCT/FR01/00241

§ 371 (c)(1), (2), (4) Date: Jul. 15, 2002

(87) PCT Pub. No.: WO01/55122

PCT Pub. Date: Aug. 2, 2001

(65) Prior Publication Data

US 2003/0109530 A1 Jun. 12, 2003

(30) Foreign Application Priority Data

Jan. 26, 2000 (FR) .............................. 00 00996

(51) Int. Cl.
 C07D 251/10 (2006.01)
 A61K 31/53 (2006.01)
 A61P 3/06 (2006.01)
 A61P 3/10 (2006.01)

(52) U.S. Cl. .................. 514/245; 544/204; 544/206; 544/208; 544/209

(58) Field of Classification Search ............ 544/204, 544/206, 208, 209; 514/245
See application file for complete search history.

(56) References Cited

U.S. PATENT DOCUMENTS 3,287,366 A  11/1966  Newman et al.

FOREIGN PATENT DOCUMENTS

| JP | 48 064088 | 9/1973 |
| JP | 54 014986 | 2/1979 |
| WO | 99 31088 | 6/1999 |

OTHER PUBLICATIONS

"Journal of Medicinal Chemistry, US, American Chemical Society, Washington," vol. 6, No. 4, pp. 370–378, 1963.

Stevens et al., "Introduction of a triflate group into sterically hindered positions in 1–aryl–4,6–diamino–1,3,5–triazines and their Dimroth rearrangement products," Journal of Heterocyclic Chemistry, vol. 30, No. 4, pp. 849–853, 1993.

*Primary Examiner*—Venkataraman Balasubramanian
(74) *Attorney, Agent, or Firm*—Young & Thompson

(57) ABSTRACT

The invention concerns compounds of general formula (I) wherein: R1, R2, R3, R4, R5 and R6 are as defined in Claim 1. Said compounds are useful in the treatment of pathologies related to the insulin-resistance syndrome.

11 Claims, No Drawings

DIHYDRO-1,3,5-TRIAZINE AMINE DERIVATIVES AND THEIR THERAPEUTIC USES

The present invention relates to amine-containing derivatives of dihydro-1,3,5-triazine which are useful in the treatment of pathological conditions associated with the insulin-resistance syndrome.

Amine-containing derivatives of dihydro-1,3,5-triazine having hypoglycaemic properties have been described in JP-A-73 64 088 and JP-A-79 14 986.

The aim of the present invention is to provide novel compounds having improved properties.

The subject of the present invention is thus a compound of general formula (I):

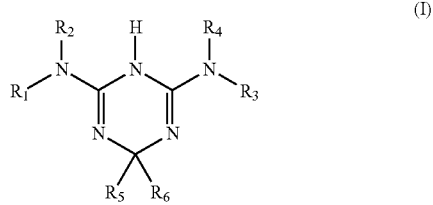

in which:

R1, R2, R3 and R4 are chosen independently from the groups:
  H,
  (C1–C20)alkyl substituted or otherwise with halogen, (C1–C5)alkyl, (C1–C5)alkoxy, (C3–C8)cycloalkyl,
  (C2–C20)alkylene substituted or otherwise with halogen, (C1–C5)alkyl, (C1–C5)alkoxy,
  (C2–C20)alkyne substituted or otherwise with halogen, (C1–C5)alkyl, (C1–C5)alkoxy,
  (C3–C8)cycloalkyl substituted or otherwise with (C1–C5)alkyl, (C1–C5)alkoxy,
  (C3–C8)heterocycloalkyl carrying one or more heteroatoms chosen from N, O, S and substituted or otherwise with (C1–C5)alkyl, (C1–C5)alkoxy,
  (C6–C14)aryl (C1–C20)alkyl substituted or otherwise with amino, hydroxyl, thio, halogen, (C1–C5)alkyl, (C1–C5)alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl,
  (C6–C14)aryl substituted or otherwise with amino, hydroxyl, thio, halogen, (C1–C5)alkyl, (C1–C5)alkoxy, (C1–C5)alkylthio, (C1–C5)alkylamino, (C6–C14)aryloxy, (C6–C14)aryl (C1–C5)alkoxy, cyano, trifluoromethyl, carboxyl, carboxymethyl or carboxyethyl,
  (C1–C13)heteroaryl carrying one or more heteroatoms chosen from N, O, S and substituted or otherwise with amino, hydroxyl, thio, halogen, (C1–C5)alkyl, (C1–C5)alkoxy, (C1–C5)alkylthio, (C1–C5)alkylamino, (C6–C14)aryloxy, (C6–C14)aryl-(C1–C5)alkoxy, cyano, trifluoromethyl, carboxyl, carboxymethyl or carboxyethyl, it being possible for R1 and R2, on the one hand, and R3 and R4, on the other hand, to form with the nitrogen atom an n-membered ring (n between 3 and 8) comprising or otherwise one or more heteroatoms chosen from N, O, S and being capable of being substituted with one or more of the following groups: amino, hydroxyl, thio, halogen, (C1–C5)alkyl, (C1–C5)alkoxy, (C1–C5)alkylthio, (C1–C5) alkylamino, (C6–C14)aryloxy, (C6–C14)aryl (C1–C5) alkoxy, cyano, trifluoromethyl, carboxyl, carboxymethyl or carboxyethyl, R5 and R6 are chosen independently from the groups:
  H,
  (C1–C20)alkyl substituted or otherwise with amino, hydroxyl, thio, halogen, (C1–C5) alkyl, (C1–C5) alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl,
  (C2–C20)alkylene substituted or otherwise with amino, hydroxyl, thio, halogen, (C1–C5)alkyl, (C1–C5) alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl,
  (C2–C20)alkyne substituted or otherwise with amino, hydroxyl, thio, halogen, (C1–C5)alkyl, (C1–C5) alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl,
  (C3–C8)cycloalkyl substituted or otherwise with amino, hydroxyl, thio, halogen, (C1–C5)alkyl, (C1–C5) alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl,
  (C3–C8)heterocycloalkyl carrying one or more heteroatoms chosen from N, O, S and substituted or otherwise with amino, hydroxyl, thio, halogen, (C1–C5)alkyl, (C1–C5)alkoxy, (C1–C5)alkylthio, (C1–C5) alkylamino, (C6–C14)aryloxy, (C6–C14)aryl(C1–C5) alkoxy, cyano, trifluoromethyl, carboxyl, carboxymethyl or carboxyethyl,
  (C6–C14)aryl substituted or otherwise with amino, hydroxyl, thio, halogen, (C1–C5)alkyl, (C1–C5) alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl,
  (C1–C13)heteroaryl carrying one or more heteroatoms chosen from N, O, S and substituted or otherwise with amino, hydroxyl, thio, halogen, (C1–C5)alkyl, (C1–C5)alkoxy, (C1–C5)alkylthio, (C1–C5) alkylamino, (C6–C14)aryloxy, (C6–C14)aryl(C1–C5) alkoxy, cyano, trifluoromethyl, carboxyl, carboxymethyl or carboxyethyl,
  (C6–C14)aryl(C1–C5)alkyl substituted or otherwise with amino, hydroxyl, thio, halogen, (C1–C5)alkyl, (C1–C5)alkoxy, (C1–C5)alkylthio, (C1–C5) alkylamino, (C6–C14)aryloxy, (C6–C14)aryl(C1–C5) alkoxy, cyano, trifluoromethyl, carboxyl, carboxymethyl or carboxyethyl, it being possible for R5 and R6 to form with the carbon atom to which they are attached an m-membered ring (m between 3 and 8) comprising or otherwise one or more heteroatoms chosen from N, O, S and being capable of being substituted with amino, hydroxyl, thio, halogen, (C1–C5) alkyl, (C1–C5)alkoxy, (C1–C5)alkylthio, (C1–C5) alkylamino, (C6–C14)aryloxy, (C6–C14)aryl(C1–C5) alkoxy, cyano, trifluoromethyl, carboxyl, carboxymethyl or carboxyethyl, or being capable of forming with the carbon atom a C10–C30 polycyclic residue substituted or otherwise with amino, hydroxyl, thio, halogen, (C1–C5)alkyl, (C1–C5)alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl, it being possible for the nitrogen atom of a heterocyloalkyl or heteroaryl group to be substituted with a (C1–C5)alkyl, (C3–C8)cycloalkyl, (C6–C14)aryl, (C6–C14)aryl(C1–C5)alkyl or (C1–C6)acyl group, with the exclusion of the compounds of formula I in which:

a—R1=H, R2=H, R3=H, R5=CH3, R6=CH3 and R4=phenethyl, phenoxyethyl, 2-phenylthioisopropyl or benzyl;

b—R1=H, R2=H, R3=H or CH3, R4=H, methyl, butyl or phenethyl, R5=H or ethyl and R6 is 3-methyl-5-isoxazolyl, 5-methyl-3-isoxazolyl, 3-methyl-5-pyrazolyl or (5-methyl-3-isoxazolyl)methyl, c—R1, R2, R3 and R4 represent a hydrogen atom, as well as the tautomeric, enantiomeric, diastereoisomeric and epimeric forms and the pharmaceutically acceptable salts.

The expression m-membered ring formed by R5 and R6 is understood to mean in particular a saturated ring such as a cyclohexyl, piperidinyl or tetrahydropyranyl group.

The expression polycyclic group formed by R5 and R6 is understood to mean an optionally substituted carbon-containing polycyclic group and in particular a steroid residue.

A particular group of compounds of formula (I) is that in which R5 is hydrogen.

Another particular group of compounds of formula (I) is that in which R5 and R6 form with the carbon atom to which they are attached an m-membered ring (m between 3 and 8) comprising or otherwise one or more heteroatoms chosen from N, O, S and being capable of being substituted with one or more of the following groups: (C1–C5)alkyl, amino, hydroxyl, (C1–C5)alkylamino, (C1–C5)alkoxy, (C1–C5)alkylthio, (C6–C14)aryl, (C6–C14)aryl(C1–C5)alkoxy, or form with the carbon atom a C10–C30 polycyclic residue substituted or otherwise with amino, hydroxyl, thio, halogen, (C1–C5)alkyl, (C1–C5)alkoxy, (C1–C5)alkylthio, (C1–C5)alkylamino, (C6–C14)aryloxy, (C6–C14)aryl (C1–C5)alkoxy, cyano, trifluoromethyl, carboxyl, carboxymethyl or carboxyethyl.

Another particular group of compounds of formula (I) is that in which R5 and R6 are chosen independently from the groups:

(C1–C20)alkyl substituted or otherwise with amino, hydroxyl, thio, halogen, (C1–C5)alkyl, (C1–C5) alkoxy, (C1–C5)alkylthio, (C1–C5)alkylamino, (C6–C14)aryloxy, (C6–C14)aryl(C1–C5)alkoxy, cyano, trifluoromethyl, carboxyl, carboxymethyl or carboxyethyl.

A more particular group of compounds of formula (I) is that in which R1 and R2 are chosen independently from the groups specified above with the exception of the hydrogen atom and R3 and R4 represent a hydrogen. More particularly, a preferred group of compounds of formula (I) is that in which R1 and R2 are an alkyl, advantageously methyl, group and R3 and R4 represent a hydrogen.

The invention also relates to the tautomeric, enantiomeric, diastereoisomeric and epimeric forms of the compounds of general formula (I).

The compounds of general formula (I) possess basic nitrogen atoms which may be monosalified or disalified with organic or inorganic acids.

The compounds of general formula (I) may be prepared by reacting a compound of general formula (II)

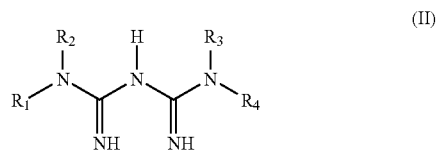

in which R1, R2, R3 and R4 are as defined above, with a compound of general formula (III), (IV) or (V)

in which R5 and R6 are as defined above and R7 is a methyl or ethyl group, in a polar solvent (for example ethanol or dimethylformamide) in the presence of an organic acid (for example camphorsulphonic acid) or of an inorganic acid (for example hydrochloric acid).

The compounds of general formula (II) are biguanides whose synthesis is routine to every person skilled in the art. We will cite for example some publications describing the synthesis of such compounds (FR 1537604, FR 2132396; K. H. Slotta and R. Tschesche, Ber., 1929 (62b), 1398; S. L. Shapiro, V. A. Parrino, E. Rogow and L. Freedman, J. Org. Chem., 1959 (81), 3725; S. L. Shapiro, V. A. Parrino and L. Freedman, J. Org. Chem., 1959 (81), 3728; S. L. Shapiro, V. A. Parrino and L. Freedman, J. Org. Chem., 1959 (81), 4636).

The compounds according to the present invention are useful in the treatment of pathological conditions associated with the insulin-resistance syndrome (X syndrome).

Insulin-resistance is characterized by a reduction in the action of insulin (cf. Presse Médicale, 1997, 26 (No. 14), 671–677) and is involved in a large number of pathological states, such as diabetes and more particularly non-insulin-dependent diabetes (type II diabetes or NIDDM), dyslatupidaemia, obesity, high blood pressure, as well as certain microvascular and macrovascular complications such as atherosclerosis, retinopathies and neuropathies.

In this regard, reference may be made for example to Diabètes, vol. 37, 1988, 1595–1607; Journal of Diabetes and its complications, 1998, 12, 110–119 or Horm. Res., 1992, 38, 28–32.

In particular, the compounds of the invention have a high hypoglycaemic activity.

The compounds according to the present invention can also be used to treat chronic complications which are in particular due to the formation of "advanced glycosylation end-products" noted AGEs which are derived from the glycoxidation reaction between glucose, its oxidation derivatives and the amino functional groups of proteins, including the so-called Maillard reactions for glycation of glyoxal for example.

Indeed, recently published data clearly show the impact of AGEs on renal complications (Nephr. Dial. Transplant., 2000, 15 (suppl 2), 7–11), on atherosclerosis, Alzheimer's disease and other neurodegenerative diseases (Glycoconj. J., 1998, 15 (10), 1039–42; Brain Res., 2001, 888(2), 256). The formation of AGE may also play an important part in the pathogenesis of angiopathy, in particular in diabetics, and also in senility (J. Neuropathol. Exp. Neurol., 2000, 59 (12), 1094).

The subject of the present invention is therefore also pharmaceutical compositions comprising, as active ingredient, a compound according to the invention.

These pharmaceutical compositons are particularly intended for treating diabetes, pathological conditions due to the formation of AGEs, such as, in particular, renal complications, atherosclerosis, angiopathy, Alzheimer's disease, neurodegenerative diseases and senility.

The pharmaceutical compounds according to the invention may be provided in forms intended for administration by the parenteral, oral, rectal, permucosal or percutaneous route.

They will therefore be provided in the form of injectable solutions or suspensions or multidose vials, in the form of uncoated or coated tablets, sugar-coated tablets, capsules, gelatin capsules, pills, cachets, powders, suppositories or rectal capsules, solutions or suspensions, for percutaneous use in a polar solvent, for permucosal use.

The excipients which are suitable for such administrations are the derivatives of cellulose or of microcrystalline cellulose, the alkaline-earth carbonates, magnesium phosphate, starches, modified starches, lactose for the solid forms.

For rectal use, cocoa butter or the stearates of polyethylene glycol are the preferred excipients.

For parenteral use, water, aqueous solutions, physiological saline, isotonic solutions are the vehicles most conveniently used.

The dosage may vary within wide limits (0.5 mg to 1 000 mg) according to the therapeutic indication and the route of administration, as well as the age and weight of the subject.

By way of example, here are a few biguanides of formula II used in the synthesis of derivatives of formula I.

TABLE I

| Formula | | Salt | m.p. in °C. (Köfler) |
|---|---|---|---|
| A | [structure: (CH$_3$)$_2$N-C(=NH)-NH-C(=NH)-NH$_2$] | HCl | 223–225 |
| B | [structure: (CH$_3$)$_2$N-C(=NH)-NH-C(=NH)-NH-CH$_2$-CH=CH$_2$] | HCl | 176–178 |
| C | [structure: (CH$_3$)$_2$N-C(=NH)-NH-C(=NH)-NH-CH(CH$_3$)$_2$] | HCl | 230–232 |

TABLE I-continued

| Formula | | Salt | m.p. in °C. (Köfler) |
|---|---|---|---|
| D | [structure: (CH$_3$)$_2$N-C(=NH)-NH-C(=NH)-NH-CH$_2$CH$_3$] | HCl | 210–212 |
| E | [structure: (CH$_3$)$_2$N-C(=NH)-NH-C(=NH)-N(CH$_3$)$_2$] | HCl | 254–256 |
| F | [structure: (CH$_3$)$_2$N-C(=NH)-NH-C(=NH)-NH-CH$_3$] | HCl | 158–160 |
| G | [structure: PhCH$_2$CH$_2$-NH-C(=NH)-NH-C(=NH)-NH$_2$] | HCl | 100–102 |

The following examples illustrate the preparation of the compounds of formula I.

EXAMPLE 1

Synthesis of 2-amino-3,6-dihydro-4-dimethylamino-6-ethyl-1,3,5-triazine hydrochloride 23 ml of propionaldehyde and 3.6 g of camphorsulphonic acid are added to a solution of compound A (25.7 g; 0.155 mol) in 200 ml of DMF. After refluxing for 2 hours, the solvent is removed under vacuum and 100 ml of acetonitrile are added. The solid formed is drained and dried (21.9 g; 69%).

m.p. =218–220° C. $^1$H NMR (DMSO-d6, 200 MHz): 1.10 (t, 3H); 1.80 (m, 2H) 3.20 (s, 6H); 4.83 (m, 1H); 7.57 (m, 2H); 8.65 (s, 1H); 8.90 (s, 1H) $^{13}$C NMR (DMSO-d6, 50 MHz): 6.41 (CH3); 27.59 (CH2); 35.64 (CH3); 60.75 (CH); 155.01 (C=N); 156.67 (C=N)

EXAMPLE 2

Synthesis of 2,4-bisdimethylamino-3,6-dihydro-6-methyl-1,3,5-triazine hydrochloride 61 ml of acetal and 5 g of camphorsulphonic acid are added to a solution of compound E (41.10 g; 0.212 mol) in 200 ml of absolute ethanol. The whole is heated under reflux for 72 hours and then concentrated. The crude material is triturated with acetonitrile and the solid formed is drained and then recrystallized from acetonitrile. 24 g (51.5%) of a solid are obtained.

m.p. =200–202° C. $^1$H NMR (DMSO-d6, 200 MHz): 1.34 (d, 3H); 3.02 (s, 6H) 4.72 (m, 1H); 4.83 (m, 1H); 8.80 (s, 2H) $^{13}$C NMR (DMSO-d6, 50 MHz): 22.59 (CH3); 37.76 (CH3); 59.02 (CH); 156.35 (C=N)

The characteristics of these compounds and of other compounds of formula I are given in Table II below:

TABLE II

| | Formula | Salt | m.p. in ° C. (Köfler) | $^{13}$C NMR 50.32 MHz |
|---|---|---|---|---|
| 1 | 6-ethyl-N,N-dimethyl-1,6-dihydro-1,3,5-triazine-2,4-diamine | HCl | 218–220 | DMSO-d6 6.41, CH3 27.59, CH2 35.64, 2 CH3 60.75, CH 155.01, 156.67, 2 quaternary C |
| 2 | N,N,N',N',6-pentamethyl-1,6-dihydro-1,3,5-triazine-2,4-diamine | HCl | 200–202 | DMSO-d6 22.58, 37.75, 5 CH3 59.01, CH 156.34, 2 quaternary C |
| 3 | N,N,6,6-tetramethyl-1,6-dihydro-1,3,5-triazine-2,4-diamine | | 193–195 | DMSO-d6 32.06, 37.40, 2 CH3 67.85, 158.16, 3 quaternary C |
| 4 | spirocyclohexyl triazine diamine | HCl | 243–245 | DMSO-d6 21.66, 25.19, 37.72, 3 CH2 37.89, 2 CH3 67.51, 156.83, 158.24, 3 quaternary C |
| 5 | N,N,6,6-tetramethyl triazine diamine | Methane-sulphonate | 174–176 | DMSO-d6 34.31, 41.36, 44.79, 5 CH3 69.75, 160.30, 161.44, 3 quaternary C |
| 6 | 6-(3-hydroxypropyl)-N,N,6-trimethyl triazine diamine | | 138–140 | DMSO-d6 28.04, CH2 30.84, 37.40, 3 CH3 42.06, 62.24, 2 CH2 70.00, 158.24, 158.69, 3 quaternary C |
| 7 | 6-(3-hydroxypropyl)-N,N,6-trimethyl triazine diamine | HCl | 150–152 | DMSO-d6 27.39, CH2 28.78, 39.14, 3 CH3 40.21, 61.30, 2 CH2 68.46, 156.48, 157.84 3 quaternary C |

TABLE II-continued

| | Formula | Salt | m.p. in °C. (Köfler) | ¹³C NMR 50.32 MHz |
|---|---|---|---|---|
| 8 | (structure: 6,6-dimethyl-N,N-dimethyl-N'-allyl-1,6-dihydro-1,3,5-triazine-2,4-diamine) | HCl | 124–126 | DMSO 28.95, 38.65, 2 CH3 42.77, CH2 69.75, quaternary C 115.93, CH2 149.12, CH 155.70, 156.16, 2 quaternary C |
| 9 | (structure: 6,6-dimethyl-N,N-dimethyl-N'-isopropyl-1,6-dihydro-1,3,5-triazine-2,4-diamine) | HCl | 149–151 | DMSO-d6 26.20, 32.39, 40.73, 6 CH3 46.16, CH 60.09, 158.83, 159.14, 3 quaternary C |
| 10 | (structure: N,N-dimethyl-6-phenyl-1,6-dihydro-1,3,5-triazine-2,4-diamine) | HCl | 239–241 | DMSO-d6 37.78, 2 CH3 62.39, CH 126.66, 129.47, 5 CH 141.87, 156.52, 158.38, 3 quaternary C |
| 11 | (structure: N,N-dimethyl-6-(4-methoxyphenyl)-1,6-dihydro-1,3,5-triazine-2,4-diamine) | HCl | 221–223 | DMSO-d6 37.23, 55.60, 3 CH3 61.88, CH 114.32, 127.66, 4 CH 133.17, 156.11, 157.86, 159.93, 4 quaternary C |
| 12 | (structure: N,N-dimethyl-6-(4-hydroxyphenyl)-1,6-dihydro-1,3,5-triazine-2,4-diamine) | HCl | 251–253 | DMSO-d6 37.75, 2 CH3 62.67, 116.16, 128.16, 5 CH 131.72, 156.64, 158.31, 158.88, 4 quaternary C |

TABLE II-continued

| | Formula | Salt | m.p. in °C. (Köfler) | ¹³C NMR 50.32 MHz |
|---|---|---|---|---|
| 13 | | | >260 | DMSO-d6 39.55, 39.71, 2 CH3 65.92, 117.71, 130.17, 5 CH 131.72, 156.64, 158.31, 158.88, 4 quaternary C |
| 14 | | Fumarate | 172–174 | 15.48, 29.33, 3 CH3 35.68, CH2 37.43, 2 CH3 65.71, quaternary C 135.47, 2 CH 156.21, 156.63, 168.35, 4 quaternary C |
| 15 | | HCl | 250–252 | DMSO-d6 28.74, 37.38, 6 CH3 66.53, 155.28, 3 quaternary C |
| 16 | | HCl | 183–185 | DMSO-d6 32.62, 40.96, 5 CH3 69.37, 159.30, 160.19, 3 quaternary C |
| 17 | | HCl | >260 | DMSO-d6 22.78, 2 CH3 28.96, 2 CH2 40.13, 2 CH3 42.73, 2 CH2 65.63, 155.42, 155.71, 3 quaternary C |
| 18 | | HCl | 229–231 | DMSO-d6 22.97, 37.76, 3 CH3 58.59, CH 157.85, 159.39, 2 quaternary C |

TABLE II-continued

| Formula | Salt | m.p. in ° C. (Köfler) | ¹³C NMR 50.32 MHz |
|---|---|---|---|
| 19 (cholestane-substituted triazine with N(CH₃)₂ and NH₂) | HCl | >260 | Concise spectrum DMSO-d6 69.06, 159.78, 161.17, 3 quaternary C |
| 20 (phenethylamino-NH₂ triazine spirocyclohexane) | carbonate | 170–180 | CF3CO2D 22.43, 25.71, 36.86, 38.71, 43.12, 7 CH2 67.88, quaternary C 127.47, 129.55, 129.93, 5 CH 140.22, 158.72, 159.65, 3 quaternary C |
| 21 (N,N-dimethyl, pyrrolidinyl, CH₃-substituted triazine) | Carbonate | >140 | DMSO-d6 20.51, CH3 24.73, 25.39, 2 CH2 39.98, 2 CH3 46.44, 47.91, 2 CH2 58.49, CH 154.58, 156.63, 160.61, 3 quaternary C |
| 22 (N,N-dimethyl, N-methyl triazine spirocyclohexane) | HCl | >260 | DMSO-d6 21.18, 24.68, 3 CH2 27.26, CH3 37.00, 2 CH2 37.37, 2 CH3 67.12, 155.89, 156.86, 3 quaternary C |
| 23 (N,N-dimethyl, N-ethyl triazine spirocyclohexane) | HCl | 248–250 | DMSO-d6 15.11, CH3 21.17, 24.70, 35.39, 37.04, 6 CH2 37.36, 2 CH3 67.09, 155.90, 156.21, 3 quaternary C |

TABLE II-continued

| | Formula | Salt | m.p. in ° C. (Kofler) | 13C NMR 50.32 MHz |
|---|---|---|---|---|
| 24 | | HCl | >260 | Concise spectrum DMSO-d6 67.46, 68.80, 156.76, 157.47, 157.99, 159.14, 3 quaternary C 175.90, 176.11, COOH |
| 25 | | HCl | >260 | Concise spectrum DMSO-d6 64.87, 69.85, 2 CHOH 66.55, 154.91, 156.19, 3 quaternary C 173.75, COOH |
| 26 | | HCl | 91—93 | DMSO-d6 25.76, 37.28, 3 CH3 43.28, CH2 64.27, CH 115.21, CH2 137.55, CH 159.79, 160.77, 2 quaternary C |
| 27 | | HCl | >260 | DMSO-d6 25.69, 27.25, 4 CH2 39.13, 2 CH3 67.25, quaternary C 70.01, CH2 72.50, CH 128.17, 128.34, 129.07, 5 CH 139.79, 156.81, 158.30, 3 quaternary C |
| 28 | | HCl | >250 | DMSO-d6 29.83, 34.4, 4 CH2 38.83, 2 CH3 66.17, CH 67.06, 156.25, 157.28, 3 quaternary C |

TABLE II-continued

| | Formula | Salt | m.p. in ° C. (Köfler) | $^{13}$C NMR 50.32 MHz |
|---|---|---|---|---|
| 29 | | Carbonate | 133–135 | DMSO-d6 7.25, 26.81, 2 CH3 34.32, CH2 37.17, 2 CH3 68.59, 156.46, 157.71, 160.78, 4 quaternary C |
| 30 | | Carbonate | 140–144 | 8.68, 2 CH3 34.54, 2 CH2 37.91, 2 CH3 74.98, 157.84, 159.14, 160.82, 4 quaternary C |
| 31 | | HCl | 207–209 | DMSO-d6 22.50, 2 CH2 38.00, 2 CH3 39.78, 2 CH2 75.51, 157.18, 158.37, 3 quaternary C |
| 32 | | Carbonate | decomposes | DMSO-d6 14.55, CH3 17.20, CH2 37.45, 2 CH3 39.00, CH2 62.43, CH 157.52, 159.04, 160.65, 3 quaternary C |
| 33 | | HCl | >260 | D2O 37.90, 2 CH3 48.69, CH2 154.82, 156.33, 2 quaternary C |
| 34 | | Para-toluene-sulphonate | 201–203 | DMSO-d6 21.65, CH3 25.95, 26.07, 26.58, 26.89, 27.50, 5 CH2 37.56, 2 CH3 44.74, 66.56, 126.32, 129.08, 6 CH 138.99, 145.86, 158.18, 156.86, 4 quaternary C |

TABLE II-continued

| | Formula | Salt | m.p. in °C. (Köfler) | ¹³C NMR 50.32 MHz |
|---|---|---|---|---|
| 35 | (structure) | HCl | 157–159 | DMSO-d6 29.10, 37.86, 4 CH3 65.90, 154.82, 156.33, 3 quaternary C |
| 36 | (structure) | Para-toluene-sulphonate | 251–253 | DMSO-d6 21.14, 37.26, 3 CH3 114.80, 120.70, 126.41, 132.12, CF3 125.82, 128.54, 4 CH 138.37, 145.49, 155.78, 157.18, 4 quaternary C |
| 37 | (structure) | Para-toluene-sulphonate | 159–161 | DMSO-d6 21.17, 36.95, 3 CH3 42.60, CH2 62.10, 126.86, 127.21, 128.55, 128.63, 130.32, 10 CH 135.14, 138.30, 145.67, 156.18, 157.44, 5 quaternary C |
| 38 | (structure) | HCl | >260 | DMSO-d6 37.41, 2 CH3 37.47, 62.73, 4 CH2 64.76, 156.35, 157.77, 3 quaternary C |
| 39 | (structure) | HCl | >260 | DMSO-d6 34.12, 2 CH2 38.63, 42.60, 3 CH3 48.72, 2 CH2 64.01, 156.11, 157.78, 3 quaternary C |
| 40 | (structure) | HCl | 225–227 | DMSO-d6 37.19, 2 CH3 56.58, 107.94, 110.93, 144.00, 4 CH 152.78, 155.85, 157.47, 3 quaternary C |

TABLE II-continued

| | Formula | Salt | m.p. in °C. (Kofler) | $^{13}$C NMR 50.32 MHz |
|---|---|---|---|---|
| 41 | (structure: 2-amino-4-(dimethylamino)-6-(phenoxymethyl)-dihydrotriazine) | Para-toluene-sulphonate | 194–196 | DMSO-d6 21.17, 37.03, 3 CH3 60.37, CH 70.05, CH2 115.08, 121.60, 125.84, 128.54, 129.95, 10 CH 138.28, 145.64, 156.40, 157.70, 158.45, 5 quaternary C |
| 42 | (structure: 2-amino-4-(dimethylamino)-6-tert-butyl-dihydrotriazine) | HCl | >260 | DMSO-d6 24.12, 37.15, 5 CH3 39.90, quaternary C 68.39, CH 156.57, 158.10, 2 quaternary C |
| 43 | (structure: 2-amino-4-(dimethylamino)-6-isobutyl-dihydrotriazine) | HCl | decomposes | DMSO-d6 22.95, 23.05, 2 CH3 25.87, CH 36.94, 2 CH3 45.71, CH2 62.38, CH 157.15, 157.42, 158.34, 3 quaternary C |
| 44 | (structure: 2-amino-4-(dimethylamino)-6-isopropyl-dihydrotriazine) | HCl | 213–215 | DMSO-d6 15.99, 17.12, 2 CH3 34.57, CH 37.17, 2 CH3 65.68, CH 156.45, 158.12, 2 quaternary C |
| 45 | (structure: 2-amino-4-(dimethylamino)-6-(cyclohex-3-enyl)-dihydrotriazine) | Para-toluene-sulphonate | 217–219 | DMSO-d6 21.17, CH3 22.53, 24.48, 25.30, 3 CH2 37.20, 2 CH3 40.07, 64.37, 2 CH 125.68, 125.83, 127.19, 128.61, 6 CH 138.53, 145.24, 156.06, 157.36, 4 quaternary C |

Results of pharmacological studies will be given below.

Study of the Antidiabetic Activity in the Nostz Rat

The antidiabetic activity of the compounds of formula (I) administered orally was determined on an experimental model of non-insulin-dependent diabetes induced in rats by Streptozotocin.

The non-insulin-dependent diabetes model is obtained in rats by neonatal injection (on the day of birth) of streptozotocin.

The diabetic rats used were 8 weeks old. The animals were kept, from the day of their birth to the day of the experiment, in an animal house at a controlled temperature of 21 to 22° C. and subjected to a fixed cycle of light (from 7 am to 7 pm) and darkness (from 7 pm to 7 am). Their diet consisted of a maintenance diet, water and food were provided "ab libitum", with the exception of the 2 hours of fasting preceding the tests when the food is withdrawn (postabsorptive state).

The rats were treated by the oral route for one (D1) or four (D4) days with the product to be tested. Two hours after the last administration of the product and 30 minutes after anaesthetizing the animals with sodium pentobarbital (Nembutal®), 300 μl of blood sample are collected from the end of the tail.

By way of example, results obtained are assembled in Table III. These results show the efficacy of the compounds of formula (I) in reducing glycaemia in the diabetic animals. These results are expressed as a percentage variation of glycaemia at D1 and D4 (number of days of treatment) relative to D0 (before the treatment).

TABLE III

| Compounds | 20 mg/kg/D | | 200 mg/kg/D | |
|---|---|---|---|---|
| | D1 | D4 | D1 | D4 |
| 1 | −7 | −2 | −13 | −15 |
| 2 | −11 | −10 | −12 | −12 |
| 3 | −10 | −8 | −18 | −22 |
| 4 | 0 | −1 | −20 | −10 |
| 7 | −8 | −11 | −10 | −16 |
| 15 | −8 | −9 | −4 | −5 |
| 17 | −12 | −8 | −8 | −14 |
| 18 | −6 | −4 | −29 | −28 |
| 19 | −10 | −6 | −4 | −14 |
| 21 | −7 | −2 | −21 | −24 |
| 22 | −23 | −16 | −13 | 0 |
| 25 | −4 | −11 | −7 | −6 |
| 26 | −6 | −11 | −14 | −9 |
| 27 | −14 | −9 | −12 | −13 |
| 28 | −4 | −1 | −4 | −13 |
| 31 | −5 | −11 | −3 | −15 |
| 32 | 2 | 0 | −22 | −18 |
| 33 | −7 | −6 | −9 | −14 |
| 34 | −5 | −15 | −6 | −21 |
| 37 | −7 | −8 | −10 | −15 |
| 39 | −6 | −6 | −4 | −7 |
| 40 | −8 | −12 | −18 | −18 |
| 42 | −5 | −4 | −26 | −17 |
| 43 | −4 | −16 | −12 | −17 |
| 44 | −7 | −6 | −22 | −25 |

Study of the Antiglycation Activity

The compounds (1) are also capable of inhibiting the so-called Maillard reactions by "capturing effect" on the α-dicarbonyl-containing derivatives such as glyoxal—this is the antiglycation effect. This Maillard reaction inhibiting effect of the compounds according to the invention was studied in vitro by assaying ketamines ("fructosamines") produced during the incubation of albumin with methylglyoxal in the presence or otherwise of a compound of formula (I) according to the invention.

A solution of bovine albumin at 6.6 mg/ml in 0.2 M phosphate buffer, pH 7.4, is incubated with 1 mM methylglyoxal in the presence or otherwise of a compound according to the invention at a concentration of 10 mM. The incubation is carried out under sterile conditions at 37° C. for 6 days. At the end of the incubation period, the quantity of ketamines is measured with a commercially available fructosamine assay kit ("FRA" kit, product reference: 0757055, Roche S. A. products) according to the manufacturer's instructions.

By way of example, results obtained under these experimental conditions are assembled in Table IV: level of fructosamine after incubation of the albumin with the methylglyoxal in the presence of compounds (I) according to the invention in relation to the level of fructosamine when albumin is incubated with methylglyoxal in the absence of the compounds (I) according to the invention.

TABLE IV

| Compounds (I) | Reduction in the level of fructosamines (%) |
|---|---|
| 1 | 62 |
| 10 | 80 |
| 11 | 89 |
| 12 | 90 |
| 13 | 95 |
| 18 | 69 |
| 33 | 79 |
| 34 | 64 |
| 36 | 66 |
| 37 | 65 |
| 40 | 66 |
| 43 | 68 |
| 45 | 67 |

What is claimed is:

1. A compound of general formula (I):

$$\begin{array}{c} R_2 \quad H \quad R_4 \\ | \quad | \quad | \\ R_1-N \quad N \quad N-R_3 \\ \diagdown \quad \diagup \\ N \quad N \\ | \quad | \\ R_5 \quad R_6 \end{array}$$

in which:
R1, R2, are chosen independently from the groups:
H,
(C1–C20)alkyl
wherein R3, R4, are chosen independently from the groups:
H,
$(C_1-C_{20})$ alkyl
$(C_2-C_{20})$ alkenyl
R3 and R4 can form with the nitrogen atom an n-membered ring (n between 3 and 8) optionally comprising one or more heteroatoms chosen from N, O, S,
R5 and R6 are chosen independently from the groups:
H,
(C1–C20)alkyl optionally substituted with hydroxyl,
(C3–C8)cycloalkyl optionally substituted with (C6–C14)aryl (C1–C5) alkoxy,
(C3–C8)heterocycloalkyl carrying one or more heteroatoms chosen from N, O, S,
(C6–C14)aryl optionally substituted with hydroxyl,
(C1–C13)heteroaryl carrying one or more heteroatoms chosen from N, O, S,
(C6–C14) aryl (C1–C5)alkyl,
wherein R5 and R6 can form with the carbon atom to which they are attached an m-membered ring (m between 3 and 8 ) optionally comprising one or more heteroatoms chosen from N, O, S and being capable of being substituted with hydroxyl, (C1–C5)alkyl, (C6–C14)aryl (C1–C5)alkoxy,
wherein when R1 and R2 represent a hydrogen, or R3 and R4 represent a hydrogen, then R3 and R4 or R1 and R2 are defined as above with the exception of hydrogen, or its tautomeric, enantiomeric, diastereoisomeric and epimeric form or the pharmaceutically acceptable salt thereof.

2. The compound of formula (I) according to claim 1, in which R5 is hydrogen.

3. The compound of formula (I) according to claim 1, in which R5 and R6 form with the carbon atom to which they are attached an m-membered ring (m between 3 and 8) optionally comprising one or more heteroatoms chosen from N, O, S and which can be (C1–C5)alkyl.

4. The compound of formula (I) according to claim 1, in which R5 is a (C2–C20)alkyl group substituted with hydroxyl.

5. The compound of formula (I) according to claim 1, in which R5 and R6 are chosen from (C1–C20)alkyl groups optionally substituted with hydroxyl.

6. The compound of formula (I) according to claim 1 in which R1 and R2 are chosen independently from the groups specified in claim 1 with the exception of the hydrogen atom and R3 and R4 represent a hydrogen.

7. The compound of formula (I) according to claim 6, in which R1 and R2 are a methyl group and R3 and R4 represent a hydrogen.

8. The method for preparing a compound according to claim 1 comprising reacting a compound of general formula (II)

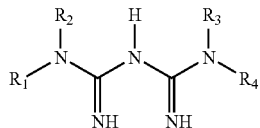

in which R1, R2, R3 and R4 are as defined above, with a compound of general formula (III), (IV) or (V)

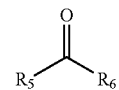 (III)

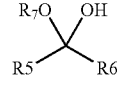 (IV)

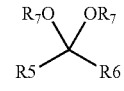 (V)

in which R5 and R6 are as defined above and R7 is a methyl or ethyl group, in a polar solvent in the presence of an organic or inorganic acid.

9. A pharmaceutical composition comprising, as active ingredient, therapeutically effective amount of a compound according to claim 1.

10. A method for the treatment of diabetes comprising administering to a patient in need thereof an effective amount of a compound according to claim 1.

11. A method for treating pathological conditions selected from the group consisting of dyslilpidaemia, obesity, high blood pressure, atherosclerosis, retinopathies and neuropathies, comprising administering to a patient in the need thereof an effective amount of a compound according to claim 1.

* * * * *